United States Patent
Giordano et al.

(10) Patent No.: US 6,765,097 B1
(45) Date of Patent: Jul. 20, 2004

(54) PROCESS FOR THE PREPARATION OF ARYL-PYRIDINYL COMPOUNDS

(75) Inventors: Claudio Giordano, Milan (IT); Claudio Pozzoli, Monza (IT); Fabio Benedetti, Cremella (IT)

(73) Assignee: Euticals Prime European Therapeutical SpA, Lodi (IT)

( * ) Notice: Subject to any disclaimer, the term of this patent is extended or adjusted under 35 U.S.C. 154(b) by 57 days.

(21) Appl. No.: 10/110,685

(22) PCT Filed: Oct. 10, 2000

(86) PCT No.: PCT/IT00/00404
§ 371 (c)(1),
(2), (4) Date: Apr. 11, 2002

(87) PCT Pub. No.: WO01/27083
PCT Pub. Date: Apr. 19, 2001

(30) Foreign Application Priority Data

Oct. 12, 1999 (IT) .......................... MI99A2127

(51) Int. Cl.$^7$ ............................ C07D 213/46
(52) U.S. Cl. ....................................... 546/340
(58) Field of Search ........................ 546/340

(56) References Cited

U.S. PATENT DOCUMENTS

| | | |
|---|---|---|
| 6,169,184 B1 | 1/2001 | Hamprecht et al. |
| 6,248,892 B1 | 6/2001 | Noerenberg et al. |

FOREIGN PATENT DOCUMENTS

| | | |
|---|---|---|
| DE | 196 36 995 A1 | 3/1998 |
| EP | 0 972 765 A1 | 1/2000 |
| WO | WO 97/40029 | 10/1997 |

OTHER PUBLICATIONS

Green, T.W. et al., Acetals and Ketals, *Protective Groups in Organic Synthesis*, 3$^{rd}$ ed., John Wiley & Sons, 1999, pp. 297–329.

Jetter, Michele C. et al., "Synthesis of 4–Substituted Imidazoles via Palladium–Catalyzed Cross–Coupling Reactions", Synthesis, Jun. 1998, pp. 829–831.

Miller, Joseph A. et al., "Synthesis of Functionally Substituted Unsymmetrical Biaryls via a Novel Double Metal Catalyzed Coupling Reaction", *Tetrahedron Letters 39* (1998), pp. 7275–7278.

*Primary Examiner*—Patricia L. Morris
(74) *Attorney, Agent, or Firm*—Perkins Coie LLP; David Bogart Dort; Paul L. Hickman

(57) ABSTRACT

A process is described for the preparation of arylpyridine compounds by aryl-aryl cross-coupling reactions between a halopyridine and an arylmagnesium halide carried out in the presence of a catalytic amount of a zinc salt and a catalytic amount of palladium. The zinc salt is preferably selected from $ZnCl_2$, $ZnBr_2$ and/or $Zn(OAc)_2$, while the palladium is preferably used in the form of $Pd(PPh_3)_4$ or $Pd(OAc)_2$ +4 $PPh_3$. The reaction can also be carried out in the presence of bidentate phosphines, such as, for example, 1,3-bis(diphenylphosphine)propane or 1,4-bis(diphenylphosphine)-butane. It is thus possible to obtain molar yields higher than 97% (calculated relative to the halopyridine) and a catalyticity of more than 2000.

24 Claims, No Drawings

PROCESS FOR THE PREPARATION OF ARYL-PYRIDINYL COMPOUNDS

Arylpyridines are generally used in organic synthesis as intermediates for the preparation of various kinds of compound; of these, 4-(2'-pyridyl)benzaldehyde is a useful intermediate in the preparation of antiviral drugs and, in particular, of HIV protease inhibitors, such as, for example, the azahexane heterocyclic derivatives described in international patent application WO 97/40029, which is incorporated herein by reference; among the antiviral drugs concerned, one of particular interest is, for example, that indicated by the abbreviation BMS-232632 in *Drugs of the Future* 1999, 24(4):375, the structural formula of which is given below:

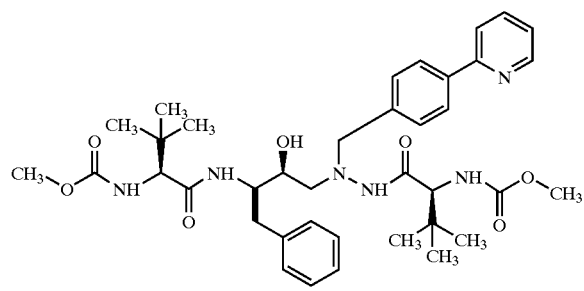

Arylpyridines can be prepared by aryl-aryl cross-coupling reactions (Lohse et al.; *Synlett.* 1999, Vol. 1; 45–48. Minato et al., *Tetrahedron Letters*, Vol. 22, no. 52, pp. 5319–5322. 1981. Ei-ichi Negishi et al. *Heterocycles* 1982, Vol. 18; 117–122), or coupling reactions between two aryl compounds in accordance with the scheme given below:

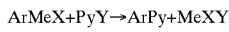

wherein:

Ar represents an aryl compound and Py represents a pyridine compound; Me represents a metal selected from Mg, Zn and Sn, and X represents Br, Cl, I; or, alternatively, Me and X, together, represent $B(OH)_2$ or $BR_2$ (wherein R is an alkyl group); Y represents Br, Cl or I.

In particular, 4-(2'-pyridyl)benzaldehyde is normally prepared starting from 4-bromobenzaldehyde and 2-bromopyridine (Bold et al.; *J.Med.Chem.* 1998, 41, 3387 and WO 97/40029), according to the scheme given in FIG. 1.

Figure 1

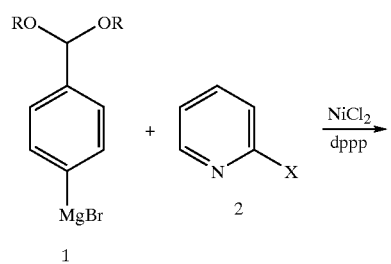

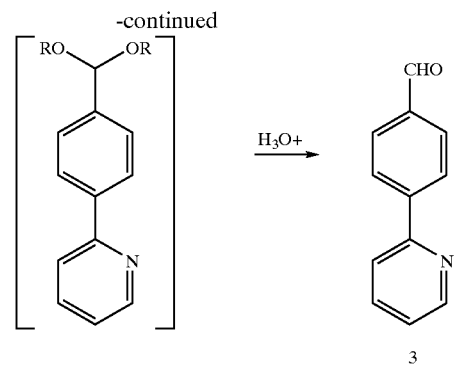

The method provides for the conversion of 4-bromobenzaldehyde into the corresponding acetal and then into the Grignard reagent $BrMgC_6H_4CH(OR)_2$ (compound 1). The Grignard reagent is then reacted with 2-bromopyridine (compound 2) in the presence of $NiCl_2$ and 1,3-bis(diphenylphosphine)propane (*Inorg. Chem.* 1966, 1968) to give, after the conversion of the acetal group into an aldehyde group, by treatment in an acidic aqueous medium, 4-(2'-pyridyl)benzaldehyde (compound 3).

However, that method has disadvantages of not inconsiderable importance, such as the use of a toxic and carcinogenic catalyst such as the nickel salt and, above all, poor reproducibility, which is all the greater the smaller the amount of catalyst employed.

The object of the work which resulted in the present invention was therefore to find a novel and reliable aryl-aryl cross-coupling process based on the use of metals that are both other than nickel and capable of leading to the formation of arylpyridines, and in particular 4-(2'-pyridyl) benzaldehyde, with reproducible and industrially satisfactory yields, even in the presence of very small amounts of catalyst.

It has now been found that a zinc salt can be used in a catalytic amount and in combination with palladium to catalyse efficiently the formation of arylpyridines by aryl-aryl cross-coupling reactions. In particular, as will be seen hereinafter, it has been found that the zinc salt in combination with palladium catalyses with optimum yields, a high level of productivity and, above all, with a high degree of catalyticity the reactions for the synthesis of arylpyridines according to the general scheme given below

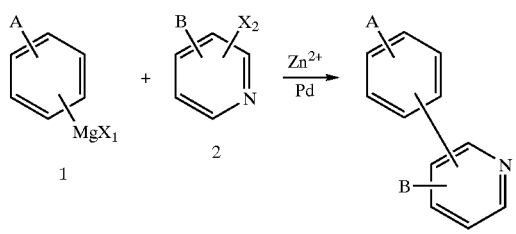

wherein A and B, which are the same or different from one another, represent H; a linear or branched $C_1$–$C_8$ alkyl; an optionally substituted acetal group; an aryl or a benzyl, which are optionally substituted by groups that do not interfere with a Grignard reaction; and $X_1$ and $X_2$, which are the same or different from one another, represent Cl, Br or I.

The subject-matter of the present invention is particularly interesting bearing in mind that coupling reactions catalysed by palladium and mediated by zinc salts have already been described in Jetter et al., *SYNTHESIS*, June 1998, 829–831. However, in that article the zinc salt was used in amounts of approximately 2 equivalents with final yields of 70–80%; by increasing the concentration of the zinc salt to 3 equivalents it was possible to obtain a substantial increase in the yield which, however, fell by 40% when only one equivalent of the zinc salt was used.

With the present invention, it has, however, surprisingly been found that the use of a catalytic amount of the zinc salt in the presence of a catalytic amount of palladium leads to the formation of arylpyridines with yields ranging from 84 to 99.5%, depending on the conditions, and also to a substantial reduction in the amount of catalyst; in this connection, among other things, it was also observed that, in the presence of a catalytic amount of the zinc salt, the palladium can be used in an amount of up to 1 mole for every 10,000 moles of arylpyridine product, which is undoubtedly surprising bearing in mind that, in the already mentioned WO 97/40029, the catalyticity was approximately 0.6 mole of nickel per 100 moles of bromopyridine. It is important to remember that the extremely high cost of palladium makes its use in an industrial process economically disadvantageous if it is employed in molar ratios with respect to the substrate of from 1:20 to 1:200.

In this connection, it should be noted that the use of catalytic amounts of zinc salts in combination with catalysts based on nickel or palladium had already been described by Miller and Farrell in *Tetrahedron Letters,* Vol. 39, 1998, 7275–8, and in the corresponding U.S. Pat. No. 5,922,898. However, those documents describe a method which permits the coupling of Grignard compounds with aryl halides containing groups reactive towards the Grignard compounds, such as, for example, esters, ketones and nitrites, the presence of the zinc salt as a co-catalyst in this case makes it possible to avoid the protection and deprotection of the groups reactive towards the Grignard compounds. In the documents in question, the ratio of the catalyst (Pd or Ni) to the aryl halide is normally approximately 1:20 and, in any case, is never less than 1:100; those documents also give examples demonstrating a high degree of inhibition of the coupling reaction in the presence of a molar ratio of 1:1 between the arylmagnesium reagent and $ZnCl_2$. The fairly high yields are also promoted by the presence of electron-attracting groups on the aryl halides, which increases the reactivity thereof in the aryl-aryl cross-coupling reactions (V. V. Grushin, H. Alper *Chem. Rev.,* 1994, 94, 1047–1062).

In contrast, the subject-matter of the present invention is represented by a process for the preparation of arylpyridines in which an arylmagnesium halide is reacted with a halopyridine in the presence of a catalytic amount of a zinc salt and a catalytic amount of palladium, wherein the molar ratio of the palladium to the halopyridine is less than 1:100 and, normally, less than 1:1000.

In order to avoid any undesired secondary reactions, the arylmagnesium halide and the halopyridine should not contain other substituents capable of interfering with the Grignard reaction or, if such substituents are present, they should be in a suitably protected form; any carbonyl groups can be protected, for example, by being converted beforehand into the corresponding acetals.

According to its preferred embodiment, the process according to the present invention can thus he represented in the following scheme.

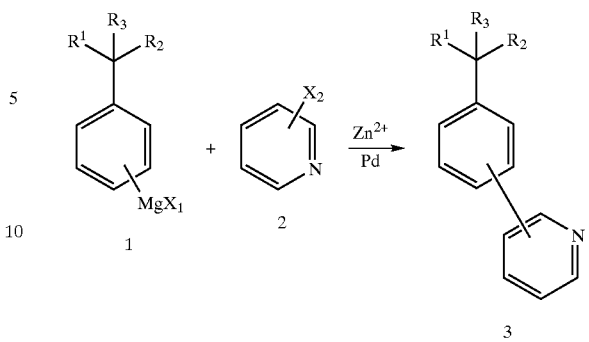

wherein: $R_1$, $R_2$ and $R_3$, which are the same or different from one another, represent H; a linear or branched $C_1$–$C_6$ alkyl; an aryl, preferably phenyl, optionally substituted by a linear or branched $C_1$–$C_6$ alkyl; or, alternatively, $R_1$ and $R_2$ represent an optionally cyclic acetal group; and $X_1$ and $X_2$, which are the same or different from one another, represent Cl, Br or I.

In its more preferred embodiment, the process consists (a) in reacting an arylmagnesium halide of formula:

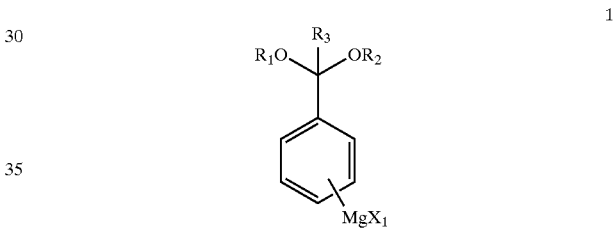

wherein $X_1$ represents Cl, Br or I; $R_1$ and $R_2$, which are the same or different from one another, represent linear or branched $C_1$–$C_6$ alkyls, preferably methyls, or alternatively, $R_1$ and $R_2$ together represent a single $C_1$–$C_8$ alkyl or alkylene group; $R_3$ represents hydrogen or a linear or branched $C_1$–$C_6$ alkyl or alkylene radical, with a halopyridine of formula:

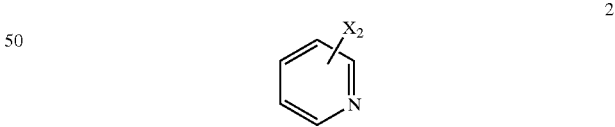

wherein $X_2$ represents Cl, Br or I, in the presence of a catalytic amount of palladium and a catalytic amount of a zinc salt, relative to which compound 1 is prerferably used in dynamic deficiency, (and the molar ratio of the palladium to the arylpyridine product being less than 1:100 and, preferably, less than 1:1000); and (b) in transforming the intermediate compound so obtained into the desired compound by converting the acetal group into a carbonyl group. In particular, it is represented by a process for the preparation of 4-(2'-pyridyl)benzaldehyde in which: (a) an arylmagnesium halide of formula:

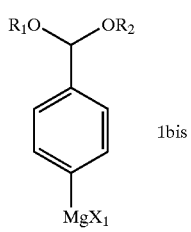

1bis wherein $X_1$, $R_1$ and $R_2$ have the meaning given above, is reacted with a halopyridine of formula:

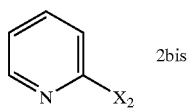

2bis wherein $X_2$ has the meaning given above, in the presence of a catalytic amount of palladium and a catalytic amount of a zinc salt, relative to which compound 1 is used in dynamic deficiency (maintaining the molar ratios of compounds 1bis to 2bis within the limits indicated above); and (b) the intermediate compound so obtained of formula:

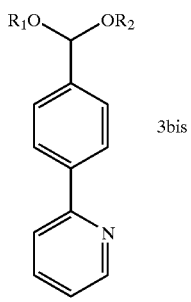

3bis is transformed into 4-(2'-pyridyl)benzaldehyde by converting the acetal group into a carbonyl group.

For the purposes of the present invention, the expression "catalytic amount" of the zinc salt means from 1 to 50 moles of zinc, preferably from 5 to 35 moles, per 100 moles of halopyridine; the expression "catalytic amount" of palladium, however, means from 0.01 to 1 mole of palladium, preferably from 0.05 to 0.1 mole, per 100 moles of halopyridine; the expression "the Grignard compound is used in dynamic deficiency relative to the zinc salt" means that the arylmagnesium halide is added dropwise to a solution already containing the halopyridine, the palladium and the zinc salt. Finally, the term "catalyticity" means the molar ratio of the catalyst to the halopyridine; owing to the fact that the process according to present invention results in an almost quantitative conversion of the halopyridine into the arylpyridine product, the "catalyticity" in practice coincides with the molar ratio of the catalyst to the arylpyridine product.

Both in its general version and in its preferred version or in its more preferred version, the molar ratio of the palladium to the halopyridine is normally from 1:3000 to 1:1000, preferably approximately 1:2000; the halopyridine is normally used in amounts of from 0.5 to 1.5 moles, preferably from 0.8 to 1.2 moles, per mole of arylmagnesium halide.

In order for the coupling reaction to take place with high yields and a high degree of selectivity in the presence of a minimum amount of catalyst, the Grignard reagent must be prevented from accumulating in the reaction medium, and must thus be in dynamic deficiency relative to the zinc salt; the amount of co-catalyst (Zn salts) necessary depends on the regularity and the speed of addition of the Grignard compound: a ratio of from 1:50 to 1:10 of the Zn salts to the halopyridine has been found to be satisfactory.

The zinc salt is generally selected from zinc chloride ($ZnCl_2$), zinc bromide ($ZnBr_2$) and zinc acetate [$Zn(OAc)_2$]. However, the palladium is used principally in the form of palladium tetrakistriphenylphosphine [$Pd(PPh_3)_4$] or palladium salts, generally acetate or chloride, and phosphines. The phosphines which can be used for this purpose are well known in the art; it is preferable to use unsubstituted phosphines, such as triphenylphosphine, or, alternatively, substituted phosphines, such as tolyl phosphines. The ratio of the palladium to the phosphines is normally one mole of palladium salt per 3–5 moles of phosphines. This reaction can also be carried out in the presence of bidentate ligands, such as, for example, bidentate phosphines, such as 1,3-bis (diphenylphosphine)propane (dppp) or 1,4-bis (diphenylphosphine)butane (dppb); the use of those ligands, in combination with palladium and the zinc salt, makes it possible to obtain molar yields higher than 97% (calculated on the halopyridine) and a catalyticity higher than 2000, using both bromopyridines and the more economical and normally less reactive chloropyridines.

The coupling reaction is generally carried out at a temperature of 25–85° C., preferably at 25–50° C., in an aprotic organic solvent that does not react with a Grignard compound, preferably in tetrahydrofuran and/or toluene.

In the more preferred embodiment of the invention, the removal of the acetal group is effected by acid hydrolysis; that is to say, stage (b) is normally carried out by treating the intermediate (for example 3bis) with an acidic aqueous solution; this stage is preferably carried out by adding an aqueous HCl solution directly to the organic solution obtained in stage (a) and by maintaining the temperature below 40° C.

It is also observed that, when the acetal group of compound 1 is obtained by reacting the corresponding carbonyl group with a $C_1$–$C_8$ diol (preferably with 1,3-propanediol, 1,2-butanediol, 1,4-butenediol or 2,2-dimethyl-1,3-propanediol), the reaction proceeds without the occurrence of secondary reactions or, at any rate, with the formation of undesired secondary products being reduced to a minimum. A further subject of the present invention is therefore represented by a compound of the general formula

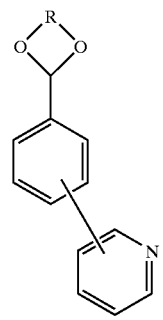

and, preferably, by a compound of formula

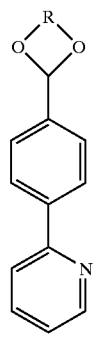

wherein R represents precisely a linear or branched $C_1$–$C_8$ alkyl or alkenyl radical; the preferred radicals are: 1,3-propyl, 1,2-butyl, 1,4-butenyl or 2,2-dimethyl-1,3-propyl.

Finally, as will be seen from the Examples, 4-(2'-pyridyl) benzaldehyde can be used for the preparation of N-1-(tert-butoxycarbonyl)-N-2-[4-(2-pyridyl)-benzyl]-hydrazine and N-1-(tert-butoxycarbonyl)-N-2-{4-[(2-pyridyl)-phenyl] methyl-idene}-hydrazone, which are more advanced intermediates which can likewise be used in the synthesis of the HIV protease inhibitors described above; further subjects of the invention are therefore represented by the procedures for the synthesis of these compounds which comprise a process for the preparation of 4-(2'-pyridyl)benzaldehyde according to the present invention.

In conclusion, the process according to the present invention permits the synthesis of arylpyridines, and in particular of 4-(2'-pyridyl)benzaldehydes, with particularly high, reproducible and industrially satisfactory yields; with a high level of productivity, with a substantially lower use of palladium compared with that described in the prior art for similar reactions, which is particularly important from the point of view of the economical nature of the process, given the extremely high cost of palladium; without the presence of electron-attracting groups on the aryl halides. These and other aspects of the invention will become clear from the following Examples which are to be regarded as non-limiting illustrations thereof.

EXAMPLES

Example 1
Preparation of the Grignard reagent of 4-bromobenzaldehyde dimethyl acetal While regulating the temperature at from 30 to 35° C., iodine (0.2 g) and then, over a period of approximately one hour, a solution of 4-bromobenzaldehyde dimethyl acetal (93 g, 0.394 mol) in tetrahydrofuran (80 g) are added to a suspension of magnesium (9.6 g, 0.394 mol) in tetrahydrofuran (68 g) maintained at 30° C. with agitation under an inert atmosphere. The reaction mixture is maintained at 35° C. with agitation for one hour. Toluene (88 g) is added to the reaction mixture.
Coupling Reaction: Preparation of 4-(2'-pyridyl) benzaldehyde Anhydrous zinc chloride (13.6 g 0.1 mol) and then 2-bromopyridine (52.8 g, 0.334 mol) are added, with agitation under an inert atmosphere, to a solution constituted by toluene (156 g) and tetrahydrofuran (132 g). Palladium tetrakistriphenylphosphine (0.204 g, 0.178 mmol) and then, over a period of two hours, the Grignard solution are added to the suspension maintained at 50° C. with agitation and under an inert atmosphere. The reaction mixture is maintained at 50° C. for approximately 30 minutes and then cooled to 25° C.

A solution constituted by water (300 g) and 30% hydrochloric acid (70 g) is added to the reaction mixture over a period of approximately 30 minutes. The mixture is maintained under agitation at 25° C.–30° C. for one hour and then the phases are separated. 30% ammonia is added to the aqueous phase up to a pH of 8, and then toluene (90 g) is added. The phases are separated, the organic phase is evaporated under vacuum to yield a residue constituted by 4-(2'-pyridyl)benzaldehyde (61.1 g, 0.334 mol; yield in moles relative to the 2-bromopyridine added: 100%; turnover of the catalyst (Pd) 1876).

IR: 1695.7 cm$^{-1}$ (aldehyde C=O stretching); M.P.: 52°–53° C.; $^1$H-NMR (300 MHz, CDCl$_3$): ppm 10.2 (1H, s); 8.8 (1H,dt, J=4.8 Hz, J=1.4 Hz); 8.25 (2H, part B of an AB system, J=7.0 Hz); 8.15 (2H, part A of an AB system, J=7.0 Hz); 7.8 (2H, AB system, J=8.6 Hz, J=1.4 Hz); 7.35 (1H,m).

The product as identified by comparison with an authentic sample prepared in accordance with Example 37b described in patent WO97/40029.

Comparative Example 2
Preparation of 4-(2'-pyridyl)benzaldehyde

Example 1 was repeated without the addition of the catalytic amount of zinc chloride. The yield in moles of 4-(2'-pyridyl)benzaldehyde relative to the 2-bromopyridine added was 1%, the turnover of the catalyst (Pd) 18.

Example 3
Preparation of 4-(2'-pyridyl)benzaldehyde

Example 1 was repeated using palladium acetate (0.040 g, 0.178 mmol) and triphenylphosphine (0.186 g, 0.712 mmol) instead of palladium tetrakistriphenylphosphine. The yield in moles of 4-(2'-pyridyl)benzaldehyde relative to the 2-bromopyridine added was 91% the turnover of the catalyst (Pd) 1707.

Example 4
Preparation of 4-(2'-pyridyl)benzaldehyde

Example 1 was repeated using palladium acetate (0.04 g, 0.178 mmol) and triphenylphosphine (0.186 g, 0.712 mmol) instead of palladium tetrakistriphenylphosphine and a different amount of anhydrous zinc chloride (18.2 g, 0.133 mol). The yield in moles of 4-(2'-pyridyl)benzaldehyde relative to the 2-bromopyridine added was 88%, the turnover of the catalyst (Pd) 1650.

Example 5
Preparation of 4-(2'-pyridyl)benzaldehyde

Example 1 was repeated using a different amount of zinc chloride (2.28 g, 0.0167 mol). The yield in moles of 4-(2'-pyridyl)benzaldehyde relative to the 2-bromopyridine added was 93%, the turnover of the catalyst (Pd) 1744.

Example 6
Preparation of 4-(2'-pyridyl)benzaldehyde

Example 1 was repeated using anhydrous zinc bromide (22.5 g, 0.10 mol) instead of zinc chloride. The yield in moles of 4-(2'-pyridyl)benzaldehyde relative to the 2-bromopyridine added was 93%, the turnover of the catalyst (Pd) 1744.

Example 7
Preparation of 2-(4'-bromophenyl)-5,5-dimethyl-1,3-dioxane

A mixture constituted by 4-bromobenzaldehyde (100 g, 0.54 mol), toluene (300 ml), monohydrated p-toluenesulphonic acid (2.79 g, 0.0162 mol) and 2.2-dimethyl-1,3-propanediol (84 g, 0.81 mol) is maintained under agitation at 125° C. for 4 hours while the water is removed by azeotropic distillation using a Florentine flask.

A 30% solution of sodium methoxide in methanol (5.8 g, 0.0324 mol) is added to the reaction mixture cooled to 30° C. The whole is cooled to 25° C. and washed with water (2×100 ml). The phases are separated and the organic phase is reduced to a residue. Heptane (137 ml) is added to the dry residue and the whole is heated at 40° C. until dissolution is complete. The whole is cooled to 10° C. to give a suspension. After filtration and evaporation of the solvent under vacuum, a residue is obtained which is constituted by 2-(4'-bromophenyl)-5,5-dimethyl-1,3-dioxane (91 g, 0.335 mol, 62%).

$^1$H-NMR (300 MHz, CDCl$_3$), ppm 0.8 (3H, s); 1.3 (3H, s); 3.65 (2H, part A of an AB system, J=10.6 Hz); 3.8 (2H, part B of an AB system, J=10.6 Hz); 5.4 (1H, s); 7.4 (2H, part A of an AB system, J=8.4 Hz); 7.5 (2H, part B of an AB system, J=8.4 Hz).

Preparation of the Grignard Reagent of 2-(4'-bromophenyl)-5,5dimethyl-1,3-dioxane While regulating the temperature at from 30 to 35° C., iodine (0.05 g) and then, over a period of approximately one hour, a solution of 2-(4'-bromophenyl)-5,5-dimethyl-1,3-dioxane (26.7 g, 0.098 mol) in tetrahydrofuran (20 g) are added to a suspension of magnesium (2.4 g, 0.0985 mol) in tetrahydrofuran (17 g) maintained at 30° C. with agitation under an inert atmosphere. The reaction mixture is maintained at 35° C. with agitation for one hour. Toluene (22 g) is added to the reaction mixture.

Coupling Reaction: Preparation of 4-(2'-pyridyl) benzaldehyde

Anhydrous zinc chloride (3.4 g, 0.025 mol) and then 2-bromopyridine (13.2 g, 0.0835 mol) are added, with agitation under an inert atmosphere, to a solution constituted by toluene (39 g) and tetrahydrofuran (33 g).

Palladium tetrakistriphenylphosphine (0.051 g, 0.0442 mmol) and then, over a period of approximately 2 hours, the Grignard solution are added to the suspension maintained at 50° C. with agitation and under an inert atmosphere. The reaction mixture is maintained at 50° C. for approximately 30 minutes and then cooled to 25° C. 2-[4'-(2-pyridyl) phenyl]-5,5-dimethyl-1,3-dioxane is obtained with a yield of 84% in moles relative to the 2-bromopyridine added. Acid hydrolysis results in the formation of 4-(2'-pyridyl) benzaldehyde with an almost quantitative yield, turnover of the catalyst (Pd) 1889.

Comparative Example 8
Preparation of 4-(2'-pyridyl)benzaldehyde

Example 7 was repeated without the addition of the catalytic amount of zinc chloride. The yield in moles of 4-(2'-pyridyl)benzaldehyde relative to the 2-bromopyridine added was 2%, turnover of the catalyst (Pd) 37.

Example 9
Preparation of the Grignard Reagent of 4-bromobenzaldehyde dimethyl acetal A chip of iodine (50 mg) and p-bromobenzaldehyde dimethyl acetal (6.8 g, 98%, 0.029 mol) are added to a suspension of magnesium filings (7.0 g, 0.287 mol) in tetrahydrofuran (109 g) maintained at 30° C. with agitation under an inert atmosphere: after a few minutes, the reaction is triggered and the internal temperature reaches 35° C. At the end of the exothermic reaction, a solution of p-bromobenzaldehyde dimethyl acetal (62.4 g, 98%, 0.262 mol) in tetrahydrofuran (64.3 g) is added over a period of 1.5 hours while regulating the temperature at from 30 to 35° C. The reaction mixture is maintained under agitation at 30° C. for one hour.

Coupling Reaction: Preparation of 4-(2'-pyridyl) benzaldehyde 2-bromopyridine (38.92 g, 0.246 mol) and palladium tetrakistriphenylphosphine (0.135 g, 0.117 mmol) are added to a mixture of ZnCl$_2$ (3.08 g, 0.0226 mol) in tetrahydrofuran (59.6 g) maintained at 50° C. with agitation under an inert atmosphere. The Grignard solution (249.5 g of solution, equal to 0.291 mol) is added dropwise over a total of 3 hours to the resulting suspension, which is still maintained at 50° C. with agitation under an inert atmosphere. The reaction mixture is maintained at 50° C. for 30 minutes and then cooled to 18° C.

A solution constituted by water (126 g) and 30% hydrochloric acid (40 g) is added to the reaction mixture, keeping the temperature of the mixture below 35° C. After 30 minutes' agitation at 25° C., toluene (44 g) is added and the phases are separated. Toluene (87 g) and 30% ammonia (42 g) are added to the aqueous phase, and the phases are separated to yield, as the organic phase, a solution of 4-(2'-pyridyl)benzaldehyde (210.8 g, HPLC strength 20.6%, equal to 43.42 g, 0.237 mol; yield in moles relative to the 2-bromopyridine added: 96.4%, turnover of catalyst (Pd): 2028).

Example 10
Preparation of 4-(2'-pyridyl)benzaldehyde

Example 9 is repeated using a different amount of ZnCl$_2$ (0.1 g, 0.73 mmol), to give a molar yield of 4-(2'-pyridyl) benzaldehyde relative to the 2-bromopyridine added of 81.2%, turnover of the catalyst (Pd) equal to 1700.

Comparative Example 11
Preparation of 4-(2'-pyridyl)benzaldehyde

A solution of the Grignard reagent of 4-bromobenzaldehyde dimethyl acetal (51.4 g of solution, equal to 0.060 mol), prepared analogously to Example 9, is added dropwise over a total of 3 hours to a solution of 2-bromopyridine (8.04 g, 0.0509 mol) and palladium tetrakistriphenylphosphine (0.29 g, 0.25 mmol) in tetrahydrofuran (24 g) maintained at 50° C. with agitation under an inert atmosphere. The reaction mixture is maintained at 50° C. for one hour and then cooled to 25° C.

A yield of 4-(2-pyridyl)benzaldehyde solution of 3.8% relative to the 2-bromopyridine added is obtained, turnover of the catalyst (Pd) 76.

Example 12
Preparation of 4-(2'-pyridyl)benzaldehyde 2-bromopyridine (8.07 g, 0.051 mol) and palladium tetrakistriphenylphosphine (0.032 g, 0.028 mmol) and then, over a total of 3 hours, a solution of the Grignard reagent of 4-bromobenzaldehyde dimethyl acetal (50 g of solution, equal to 0.058 mol), prepared analogously to Example 9, are added to a mixture of ZnCl$_2$ (7.12 g, 0.052 mol) in tetrahydrofuran (24.2 g) maintained at 50° C. with agitation under an inert atmosphere. The reaction mixture is maintained at 50° C. for 30 minutes and then cooled to 25° C.

A solution constituted by water (30 g) and 30% hydrochloric acid (9 g) is added to the reaction mixture and the mixture is maintained under agitation for 2 hours at 25° C. A portion of the solvent (30 g) is evaporated under vacuum and replaced by an equal amount of toluene and then the phases are separated. Toluene (30 g) and 30% ammonia (14 g) are added to the aqueous phase. The phases are separated to give a solution of 4-(2'-pyridyl)benzaldehyde (53.74 g, HPLC strength 16.66%, equal to 8.95 g, 0.0489 mol; yield in moles relative to the 2-bromopyridine added: 96%; turnover of the catalyst (Pd): 1920).

Example 13

Preparation of 4-(2'-pyridyl)benzaldehyde

A solution of the Grignard reagent of 4-bromobenzaldehyde dimethyl acetal (63 g of solution, containing 0.074 mol), prepared analogously to Example 9, is added dropwise over a total of 6 hours to a solution of 2-bromopyridine (7.95 g, 0.050 mol), $ZnCl_2$ (0.0071 g, 0.052 mmol) and palladium tetrakistriphenylphosphine (0.032 g, 0.028 mmol) in tetrahydrofuran (23.6 g) maintained at 50° C. with agitation under an inert atmosphere. The reaction mixture is maintained at 50° C. for 30 minutes and then cooled to 25° C.

A solution constituted by water (28 g) and 30% hydrochloric acid (9 g) is added to the reaction mixture and the mixture is maintained under agitation for 2 hours at 25° C. 30 g of solvent are evaporated under vacuum and replaced by an equal amount of toluene and then the phases are separated. Toluene (30 g) and 30% ammonia (12 g) are added to the aqueous phase. After filtering over a panel of Celite the solid at the interphase and washing the panel with toluene, the phases are separated to give a solution of 4-(2'-pyridyl)benzaldehyde (73.53 g, HPLC strength 11.1%, equal to 8.16 g, 0.0446 mol; yield in moles relative to the 2-bromopyridine added 89%; turnover of catalyst (Pd): 1620; turnover of Zn: 890).

Example 14

Preparation of 4-(2'-pyridyl)benzaldehyde 2-bromopyridine (7.90 g, 0.050 mol) and palladium tetrakistriphenylphosphine (0.029 g, 0.025 mmol) and then, at a temperature of 70° C. and over a total of 3 hours, a solution of the Grignard reagent of 4-bromobenzaldehyde dimethyl acetal (53 g of solution, containing 0.062 mol), prepared analogously to Example 9, are added to a mixture of $ZnCl_2$ (0.72 g, 0.0053 mol) in tetrahydrofuran (12.4 g) maintained under agitation under an inert atmosphere. The reaction mixture is maintained at 70° C. for 30 minutes and then cooled to 25° C.

A solution constituted by water (28 g) and 30% hydrochloric acid (10 g) is added to the reaction mixture and the mixture is maintained under agitation for 2 hours at 25° C. Toluene (30 g) and 30% ammonia (9.7 g), are added and the phases are separated to give a solution of 4-(2'-pyridyl)benzaldehyde (53.5 g, HPLC strength 17%, equal to 9.09 g, 0.049 mol; yield in moles relative to the 2-bromopyridine added: 99%, turnover of catalyst (Pd): 1960).

Example 15

Preparation of Grignard Reagent

While regulating the temperature at from 30° to 35° C., iodine (0.05 g) and then, over a period of approximately 1 hour, a solution of para-bromotoluene (16.9 g, 0.0985 mol) in tetrahydrofuran (20 g) are added to a suspension of magnesium (2.4 g, 0.0985 mol) in tetrahydrofuran (17 g) maintained at 30° C. with agitation under an inert atmosphere. The reaction mixture is maintained at 35° C. with agitation for 1 hour. Toluene (22 g) is added to the reaction mixture.

Coupling Reaction: Preparation of 4-(2'-pyridyl)toluene

Anhydrous zinc chloride (3.4 g, 0.025 mol) and then 2-bromopyridine (13.2 g, 0.0835 mol) are added, with agitation under an inert atmosphere, to a solution constituted by toluene (39 g) and tetrahydrofuran (33 g).

Palladium tetrakistriphenylphosphine (0.051 g, 0.0442 mmol) and then, over a period of 2 hours, the Grignard solution are added to the suspension maintained at 50° C. with agitation and under an inert atmosphere.

The reaction mixture is maintained at 50° C. for 30 minutes and then cooled to 25° C.

A solution constituted by water (75 g) and 30% hydrochloric acid (17.5 g) is added to the reaction mixture over a period of 30 minutes. The mixture is maintained under agitation at 25–30° C. for 1 hour and then the phases are separated.

30% ammonia is added to the aqueous phase up to a pH of 8, followed by toluene (45 g).

The phases are separated and the organic phase is evaporated under vacuum to give a residue constituted by 4-(2'-pyridyl)toluene (13.7 g, 0.08 mol—yield in moles relative to the 2-bromopyridine added: 97.1%, turnover of the catalyst (Pd): 1834).

$^1$H-NMR (300 MHz, $CDCl_3$): ppm 2.4 (3H, s); 7.2 (1H, m); 7.3 (2H, d, J=8.0 Hz); 7.75 (2H, part B of an AB system, J=6.0 Hz); 7.9 (2H, part A of an AB system, J=6.0 Hz); 8.7 (1H, dt, J=1.4 Hz, J=3.2 Hz).

The product was identified by comparison with an authentic ALDRICH sample (ALDRICH catalogue 1999–2000, page 1679, cod. 46.539-9).

Comparative Example 16

Preparation of 4-(2'-pyridyl)toluene

Example 15 was repeated but without using zinc chloride. The yield in moles of 4-(2-pyridyl)toluene relative to the 2-bromopyridine added was 9%, the turnover of the catalyst (Pd) is 170.

Example 17

Preparation of 4-(2'-pyridyl)benzaldehyde

Anhydrous zinc chloride (13.6 g, 0.10 mol) and then 2-chloropyridine (39.9 g, 0.29 mol) are added, with agitation under an inert atmosphere, to a solution constituted by toluene (156 g) and tetrahydrofuran (12 g).

Palladium tetrakistriphenylphosphine (1.77 g, 0.00153 mol) and then, over a period of 2 hours at 85° C., a solution of the Grignard reagent of 4-bromobenzaldehyde dimethyl acetal (338.6 g of solution, equal to 0.394 mol), prepared analogously to Example 1, are added to the suspension maintained at 50° C. with agitation and under an inert atmosphere. The reaction mixture is maintained at 85° C. for approximately 30 minutes and then cooled to 25° C. A solution constituted by water (300 g) and 30% hydrochloric acid (70 g) is added to the reaction mixture over a period of approximately 30 minutes. The mixture is maintained under agitation at 25° C.–30° C. for one hour and the phases are separated. 30% ammonia (32 g) is added to the underlying aqueous phase up to a pH of 8, followed by toluene (90 g).

The phases are separated and the organic phase is evaporated under vacuum to give a residue constituted by 4-(2'-pyridyl)benzaldehyde (44.6 g, 0.243 mol, yield in moles relative to the 2-chloropyridine added: 84 %, turnover of the catalyst (Pd) 160).

Example 18

Preparation of 4-(2'-pyridyl)benzaldehyde 2-chloropyridine (27.95 g, 0.246 mol), palladium acetate (0.0276 g, 0.123 mmol) and 1,3-bis(diphenylphosphine)propane (0.0509 g, 0.123 mmol) are added to a mixture of $ZnCl_2$ (1.8 g, 0.013 mol) in tetrahydrofuran (53.3 g) maintained at 50° C. with agitation under an inert atmosphere. A solution of the Grignard reagent of 4-bromobenzaldehyde dimethyl acetal (239.6 2 of solution, containing 0.279 mol), prepared analogously to Example 9, is added dropwise over a total of 3 hours to the resulting suspension, still at 50° C. and under agitation under an inert atmosphere. The reaction mixture is maintained at 50° C. for 30 minutes and then cooled to 18° C.

A solution constituted by water (126 g) and 30% hydrochloric acid (40 g) is added to the reaction mixture, keeping the temperature of the mixture below 35° C. After agitation for 1 hour at 25° C., toluene (44 g) is added and the phases are separated. Toluene (87 g) and 30% ammonia (42 g) are added to the aqueous phase and the phases are separated to give, as the organic phase, a solution of 4-(2'-pyridyl) benzaldehyde (197.1 g, HPLC strength 22.2%, equal to 43.75 g, 0.239 mol; yield in moles relative to the 2-chloropyridine added: 97%, turnover of the catalyst (Pd): 1940).

Example 19
Preparation of 4-(2'-pyridyl)benzaldehyde

Example 18 is repeated using a different amount of $ZnCl_2$ (1.0 g, 0.0073 mol), to give a molar yield relative to the 2-chloropyridine added of 97.8%, turnover of the catalyst (Pd) equal to 1974.

Example 20
Preparation of 4-(2'-pyridyl)benzaldehyde

Example 18 is repeated using a different amount of THF (114 g) in the coupling reaction and adding the Grignard reagent at 70° C. (instead of at 50° C.): a molar yield relative to the 2-chloropyridine added of 99.4% is obtained, turnover of catalyst (Pd) equal to 2075.

Example 21
Preparation of 4-(2'-pyridyl)benzaldehyde

A solution of the Grignard reagent of 4-bromobenzaldehyde dimethyl acetal (49.2 g of solution, corresponding to 0.057 mol), prepared analogously to Example 9, is added dropwise over a total of 3 hours to a mixture of 2-chloropyridine (5.82 g, 0.051 mol), $ZnCl_2$ (0.48 g, 0.00352 mol), palladium acetate (0.00582 g, 0.026 mmol), 1,4-bis(diphenylphosphine)butane (0.0115 g, 0.027 mmol) in tetrahydrofuran (26.2 g) maintained at 70° C. with agitation under an inert atmosphere. The reaction mixture is maintained at 70° C. for 30 minutes and then cooled to 25° C.

A quantitative yield of 4-(2'-pyridyl)benzaldehyde is obtained relative to the chloropyridine added, turnover of the catalyst (Pd) of 1969.

Comparative Example 22
Preparation of 4-(2'-pyridyl)benzaldehyde

Example 21 was repeated in the absence of zinc chloride. A yield in moles of 4-(2'-pyridyl)benzaldehyde of 26% was obtained relative to the 2-chloropyridine added, palladium turnover of 520.

Example 23
Preparation of 4-(2'-pyridyl)benzaldehyde 2-chloropyridine (7.17 g, 0.063 mol), palladium acetate (0.0070 g, 0.031 mmol) and 1,3-bis(diphenylphosphine) propane (0.013 g, 0.033 mmol) are added to a mixture of $ZnCl_2$ (0.42 g, 3.08 mmol) in tetrahydrofuran (13.7 g) maintained at 30° C. with agitation under an inert atmosphere. A solution of the Grignard reagent of 4-bromobenzaldehyde dimethyl acetal (80.5 g of solution, containing 0.070 mol), prepared analogously to Example 9, is added dropwise over a total of 3.5 hours to the resulting suspension, still at 30° C. and under agitation under an inert atmosphere. The reaction mixture is maintained at 30° C. for 30 minutes and then cooled to 18° C.

A solution constituted by water (32 g) and 30% hydrochloric acid (10.3 g) is added to the reaction mixture, keeping the temperature of the mixture below 35° C. After 1 hour's agitation at 25° C., toluene (11 g) is added and the phases are separated. Toluene (22 g) and 30% ammonia (11 g) are added to the aqueous phase and the phases are separated to give, as the organic phase, a solution of 4-(2'-pyridyl)benzaldehyde (48.6 g, HPLC strength 22.7%, equal to 11.0 g, 0.060 mol; yield in moles relative to the 2-chloropyridine added: 95%, turnover of the catalyst (Pd): 1941).

Example 24
Preparation of 4-(3'-pyridyl)benzaldehyde

Anhydrous zinc chloride (6.8 g, 0.05.0 moles) and then 3-bromopyridine (26.4 g, 0.167 mol) are added with agitation under an inert atmosphere, to a solution constituted by toluene (78 g) and tetrahydrofuran (66 g).

Palladium tetrakistriphenylphosphine (0.102 g, 0.089 mmol) and then, over a period of 2 hours, a solution of the Grignard reagent of 4-bromobenzaldehyde dimethyl acetal (169.3 g of solution, equal to 0.197 mol), prepared analogously to Example 1, are added to the suspension maintained at 50° C. with agitation and under an inert atmosphere.

The reaction mixture is maintained at 50° C. for 30 minutes and then cooled to 25° C.

4-(3'-pyridyl)benzaldehyde (25.6 g, 0.14 mol) is obtained with a yield of 84% in moles relative to the 3-bromopyridine added, turnover of the catalyst (Pd): 1576.

IR: 1701.6 $cm^{-1}$ (aldehyde C—O stretching)

m.p.: 52°–53° C.

$^1$H-NMR (300 MHz, $CDCl_3$): ppm 10.1 (1H, s); 8.9 (1H, d, J=2.2 Hz); 8.7 (1H, dd, J=1.6 Hz, J=4.9 Hz); 8.02 (2H, part A of an AB system, J=8.2 Hz); 7.97 (1H, ddd, J=2.2 Hz, J=7.9 Hz, J=1.6 Hz); 7.78 (2H, part B of an AB system, J=8.2 Hz); 7.45 (1H, dd, J=4.9 Hz, J=7.9 Hz)

Comparative Example 25
Preparation of 4-(3'-pyridyl)benzaldehyde

Example 24 was repeated but in the absence of zinc chloride. The yield in moles of 4-(3'-pyridyl)benzaldehyde relative to the 3-bromopyridine added was 3%, turnover of the catalyst (Pd) 56.

Example 26
Preparation of 4-(4'-pyridyl)benzaldehyde

Anhydrous zinc chloride (6.8 g, 0.050 moles) and then 4-bromopyridine (26.4 g, 0.16 mol) are added, with agitation under an inert atmosphere, to a solution constituted by toluene (78 g) and tetrahydrofuran (66 g).

Palladium tetrakistriphenylphosphine (0.102 g, 0.089 mmol) and then, over a period of 2 hours, a solution of the Grignard reagent of 4-bromobenzaldehyde dimethyl acetal (169.3 g of solution, equal to 0.197 mol) prepared analogously to Example 1, are added to the suspension maintained at 50° C. with agitation and under an inert atmosphere.

The reaction mixture is maintained at 50° C. for 30 minutes and then cooled to 25° C.

4-(4'-pyridyl)benzaldehyde (27.5 g, 0.15 mol) is obtained with a yield of 90% in moles relative to the 4-bromopyridine added, turnover of the catalyst (Pd): 1685.

Example 27
Preparation of N-1-(tert-butoxycarbonyl)-N-2-{4-[(2-pyridyl)-phenyl]-methylidene}-hydrazone A solution of 2 g (1.05 mmol) of 4-(2'-pyridyl)-benzaldehyde and 1.37 g (1 mmol) of tert-butyl carbazate in 30 ml of ethanol is agitated at 80° C. for 5 hours (after 4 hours a further 0.05 equivalent of tert-butyl carbazate is added). The reaction mixture is cooled and diluted with water; the product separates from the mixture in the form of crystals.

TLC: Rf=0.51 (methylene chloride:methanol=15:1)
$^1$H-NMR (200 MHz, CDCl$_3$): ppm 8.68 (1H, m); 8.21 (1H, s); 7.98 (2H, portion A of an AB system, J=9 Hz); 7.85 (1H, s); 7.8–7.6 (4H, m); 7.22 (1H, m); 1.53 (9H, s).

Example 28

Preparation of N-1-(tert-butoxycarbonyl)-N-2-[4-(2'-pyridyl)-benzyl]-hydrazine 2 g (6.7 mmol) of N-1-(tert-butoxycarbonyl)-N-2-{4-[(2-pyridyl)-phenyl]-methylidene}-hydrazone and 0.2 g of palladium/C 5% in 30 ml of methanol, are hydrogenated at ambient pressure and at ambient temperature for 8 hours. The catalyst is filtered and washed with methanol. The solvent is removed by distillation at reduced pressure. An oily residue is obtained which, by crystallisation from cyclohexane, provides a colourless solid having a m.p. of 77–79° C.

TLC: Rf=0.46 (methylene chloride:methanol=15:1)
$^1$H-NMR (200 MHz, CDCl$_3$): ppm 8.69 (1H, m); 7.69 (2H, d, J=2 Hz); 7.45 (2H, d, J=2 Hz); 7.8–7.65 (2H, m); 7.22 (1H, m); 4.06 (2H,s); 1.47 (9H, s).

What is claimed is:

1. A process for the preparation of 4-(2'-pyridyl) benzaldehyde comprising:

reacting an arlymagnesium halide of the formula

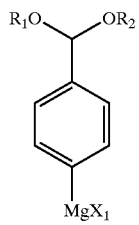

1 wherein $X_1$ represents Cl, Br or I; $R_1$ and $R_2$ which are the same or different from one another, represent linear or branched $C_1$–$C_6$ alkyls or, alternatively, $R_1$ and $R_2$ together represent a single linear or branched $C_1$–$C_6$ alkylene group, with a halopyridine of formula

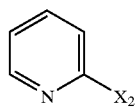

2 wherein $X_2$ represents Cl, Br, or I, in the presence of a catalytic amount of Zinc salt and a catalytic amount of Palladium, the molar ratio of the palladium to the halopyridine of formula 2 being less than 1:1000, to create an intermediate compound; and (b) converting the acetal group into a carbonyl group by acidic hydrolysis.

2. A process according to claim 1, characterized in that the arylmagnesium halide of formula 1 is used in dynamic deficiency relative to the zinc salt.

3. A process according to claim 1, characterized in that the halopyridine of formula 2 is 2-chloropyridine.

4. A process according to claim 1, characterized in that the arylmagnesium halide of formula 1 is a bromide or a chloride.

5. A process according to claim 1, characterized in that the zinc salt is selected from ZnCl$_2$, ZnBr$_2$ and/or Zn(OAc)$_2$.

6. A process according to claim 1, characterized in that the zinc salt is present in an amount of 1–50 moles per 100 moles of halopyridine.

7. A process according to claim 1, characterized in that the palladium is used in the form of Pd(PPh$_3$)$_4$ and/or Pd(OAc)$_2$+4 PPh$_3$.

8. A process according to claim 1, characterized in that the palladium is used in an amount of 0.01–1 mole per 100 moles of halopyridine.

9. A process according to claim 1, characterized in that the halopyridine of formula 2 is used in an amount of 0.8–1.2 moles, per mole of arylmagnesium halide of formula 1.

10. A process according to claim 1, characterized in that it is carried out in the presence of bidentate ligands.

11. A process according to claim 10, characterized in that the bidentate ligands are bidentate phosphines.

12. A process according to claim 11, characterized in that the bidentate phosphines are selected from 1,3-bis (diphenylphosphine)propane, 1,4-bis(diphenylphosphine) butane, and 1,1'-diphenylphosphineferrocene.

13. A process according to claim 11, characterized in that the bidentate phosphines are used in an equimolar ratio with the palladium.

14. A process according to claim 1, characterized in that stage (a) is carried out at a temperature of 0–85° C.

15. A process according to claim 1, characterized in that stage (a) is carried out in an aprotic organic solvent.

16. A process according to claim 1, characterized in that stage (b) is carried out by acid hydrolysis.

17. A process according to claim 16, characterized in that the acid hydrolysis is carried out at temperatures lower than 40° C.

18. A process according to claim 1, characterized in that $R_1$ and $R_2$ are both methyls.

19. A process according to claim 1, characterized in that $R_1$ and $R_2$, together, are selected from 1,3-propyl, 1,2-butyl, 1,4-butenyl and 2,2-dimethyl-1,3-propyl.

20. A process according to claim 1, characterized in that the molar ratio of the palladium to the halopyridine of formula 2 is from 1:3000 to 1:1000.

21. A process according to claim 6, characterzed in that the zinc salt is present in an amount of 5–30 moles per 100 moles of halopyridine.

22. A process according to claim 8, characterized in that the palladium is used in an amount of 0.05–0.1 mole per 100 moles of halopyridine.

23. A process according to claim 14, characterized in that stage (a) is carried out at a temperature of 30–50° C.

24. A process according to claim 15, characterized in that stage (a) is carried out in tetrahydrofuran and/or toluene.

* * * * *